(12) United States Patent
Nitkowski et al.

(10) Patent No.: US 9,551,650 B2
(45) Date of Patent: Jan. 24, 2017

(54) INTEGRATED OPTOFLUIDIC SYSTEM USING MICROSPHERES

(75) Inventors: Arthur Nitkowski, Ithaca, NY (US); Michal Lipson, Ithaca, NY (US)

(73) Assignee: Cornell University, Ithaca, NY (US)

( * ) Notice: Subject to any disclaimer, the term of this patent is extended or adjusted under 35 U.S.C. 154(b) by 540 days.

(21) Appl. No.: 13/375,433

(22) PCT Filed: May 28, 2010

(86) PCT No.: PCT/US2010/036625
§ 371 (c)(1),
(2), (4) Date: Apr. 18, 2012

(87) PCT Pub. No.: WO2010/141365
PCT Pub. Date: Dec. 9, 2010

(65) Prior Publication Data
US 2012/0196383 A1 Aug. 2, 2012

Related U.S. Application Data

(60) Provisional application No. 61/182,868, filed on Jun. 1, 2009.

(51) Int. Cl.
*G01N 21/77* (2006.01)
*B01L 3/00* (2006.01)
(Continued)

(52) U.S. Cl.
CPC ......... *G01N 21/05* (2013.01); *B01L 3/502715* (2013.01); *G01N 21/53* (2013.01);
(Continued)

(58) Field of Classification Search
None
See application file for complete search history.

(56) References Cited

U.S. PATENT DOCUMENTS 5,270,163 A 12/1993 Gold et al.
5,475,096 A 12/1995 Gold et al.
(Continued)

FOREIGN PATENT DOCUMENTS

WO WO-2007/051170 A2 5/2007

OTHER PUBLICATIONS

Armani, A.M. et al., "Label-free, single molecule detection with optical microcavities," Science vol. 317, No. 5839, pp. 783-787, 2007.
(Continued)

*Primary Examiner* — Erik B Crawford
*Assistant Examiner* — Gary E Hollinden
(74) *Attorney, Agent, or Firm* — Foley & Lardner LLP

(57) ABSTRACT

An integrated optofluidic system for trapping and transporting particles for analysis is provided comprising a planar substrate; a microfluidic channel; and a waveguide integrated with the channel. A microsphere particle in the integrated optofluidic system can act as a cavity, allowing light to circulate many thousands of times around the circumference of the microsphere. Optical trapping and transport is used for nanoscale positioning to excite the microsphere resonances. Sensitive measurements on molecules can be accomplished by monitoring changes in whispering gallery modes (WGMs) that propagate around the circumference of the microsphere. By using a broadband or supercontinuum light source, a microsphere can be trapped and many WGM resonances can be excited through the visible and near-infrared wavelengths simultaneously. After the resonances are measured using the waveguide transmission, the microsphere can be freed by decreasing the optical power and the process repeated with a different microsphere.

27 Claims, 16 Drawing Sheets

(51) Int. Cl.
    *G01N 21/05*     (2006.01)
    *G01N 21/53*     (2006.01)
    *G01N 21/03*     (2006.01)

(52) U.S. Cl.
    CPC .. *G01N 21/7703* (2013.01); *B01L 2400/0454* (2013.01); *G01N 21/7746* (2013.01); *G01N 2021/0346* (2013.01); *G01N 2021/058* (2013.01); *G01N 2021/7789* (2013.01)

(56) References Cited

U.S. PATENT DOCUMENTS

| | | | |
|---|---|---|---|
| 5,567,588 | A | 10/1996 | Gold et al. |
| 5,595,877 | A | 1/1997 | Gold et al. |
| 5,637,459 | A | 6/1997 | Burke et al. |
| 5,683,867 | A | 11/1997 | Biesecker et al. |
| 5,705,337 | A | 1/1998 | Gold et al. |
| 7,079,240 | B2 * | 7/2006 | Scherer et al. ............ 356/318 |
| 8,891,575 | B2 * | 11/2014 | Snee et al. ............... 372/67 |
| 2002/0168677 | A1 * | 11/2002 | Fagan .......................... 435/6 |
| 2003/0096081 | A1 | 5/2003 | Lavallee et al. |
| 2004/0091212 | A1 * | 5/2004 | Strecker et al. ............ 385/50 |
| 2005/0003520 | A1 | 1/2005 | Misiakos et al. |
| 2006/0286680 | A1 * | 12/2006 | Kang ............ G01N 21/6486 436/518 |
| 2007/0031819 | A1 | 2/2007 | Koschwanez et al. |
| 2007/0237460 | A1 * | 10/2007 | Fan et al. ................... 385/39 |
| 2009/0032730 | A1 * | 2/2009 | Erickson et al. .......... 250/435 |
| 2009/0237666 | A1 * | 9/2009 | Vollmer et al. ............ 356/432 |
| 2013/0065777 | A1 * | 3/2013 | Altug et al. ................. 506/9 |
| 2013/0130254 | A1 * | 5/2013 | Scherer et al. ............ 435/6.11 |

OTHER PUBLICATIONS

Ashkin, A. et al., "Optical trapping and manipulation of viruses and bacteria," Science, vol. 235, No. 4795. pp. 1517-1520, 1987.

Ashkin, A., "Forces of a single-beam gradient laser trap on a dielectric sphere in the ray optics regime," Biopys. J., vol. 61, No. 2, pp. 569-582, 1992.

Gaugiran S. et al., "Polarization and particle size dependence of radiative forces on small metallic particles in evanescent optical fields. Evidences for either repulsive or attractive gradient forces," Optics Express, vol. 15, pp. 8146-8156, 2007.

Gondarenko, A. et al., "High confinement micron-scale silicon nitride high q ring resonator," Opt. Express, vol. 17, No. 14, pp. 11366-11370, 2009.

International Search Report for PCT/US2010/036625 dated Dec. 29, 2010.

Kuhn, S. et al., "Loss-based optical trap for on-chip particle analysis," Lap-Chip vol. 9, No. 15, pp. 2212-2216, 2009.

Lam, C.C. et al., "Explicit asymptotic formulas for the positions, widths, and strengths of resonances in mie scattering," J. Opt. Soc. Am. B-Opt. Phys., vol. 9, No. 9, pp. 1585-1592, 1992.

Li P. et al., "Manipulation and spectroscopy of a single particle by use of white-light optical tweezers," Opt. Lett. vol. 30, No. 2, pp. 156-158, 2005.

Liu Y. et al., "Physiological monitoring of optically trapped cells: Assessing the effects of confinement by 1064-nm laser tweezers using microfluorometry," Biophys. J., vol. 71, pp. 2158-2167. 1996.

Miao, X.Y. et al., "Optical manipulation of micron/submicron sized particles and biomolecules through plasmonics, " Optics Express, vol. 16, No. 18, pp. 13517-13525, 2008.

Office Action in CN Appln No. 201080024352.0 dated Aug. 9, 2013.

Psaltis, D. et al., Developing optofluidic technology through the fusion of microfluidics and optics, Nature, vol. 442, No. 7101, pp. 381-386, 2006.

Schmidt, B.S. et al., "Optofluidic trapping and transport on solid core waveguides within a microfluidic device," Optics Express, vol. 15, No. 22, pp. 14322-14334, 2007.

Shi K.B. et al., "Broadband coherent anti-stokes raman scattering spectroscopy in supercontinuum optical trap," Appl. Phys. Lett., vol. 90, No. 14, 2007.

Vollmer, F. et al., "Protein detection by opitcal shift of a resonant microcavity," Appl. Phys. Lett., vol. 80, No. 21, pp. 4057-4059, 2002.

Yang, A.H.J. et al., "Optical manipulation of nanoparticles and biomolecules in sub-wavelength slot waveguides", Nature, vol. 457, No. 7225, pp. 71-75, 2009.

Yin D.L. et al., "Planar optofluidic chip for single particle detection, manipulation, and analysis," Lap Chip, vol. 7, No. 9, pp. 1171-1175, 2007.

Zeylikovich, I. et al., "Spectral, temporal, and coherence properties of supercontinuum generation in microstructure fiber," J. Opt. Soc, Am. B-Opt. Phys., vol. 22, No. 7, pp. 1453-1460, 2005.

\* cited by examiner

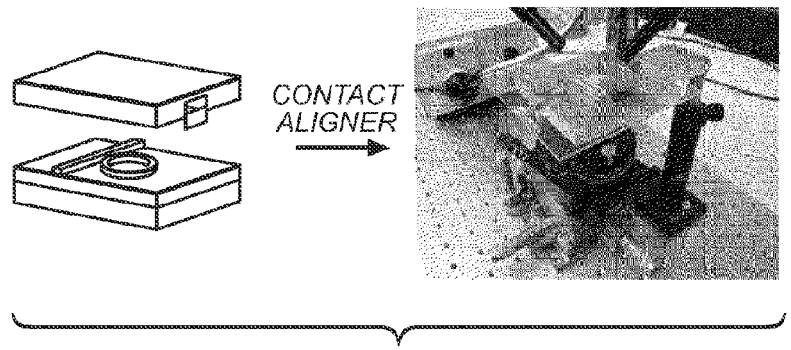
FIG. 16
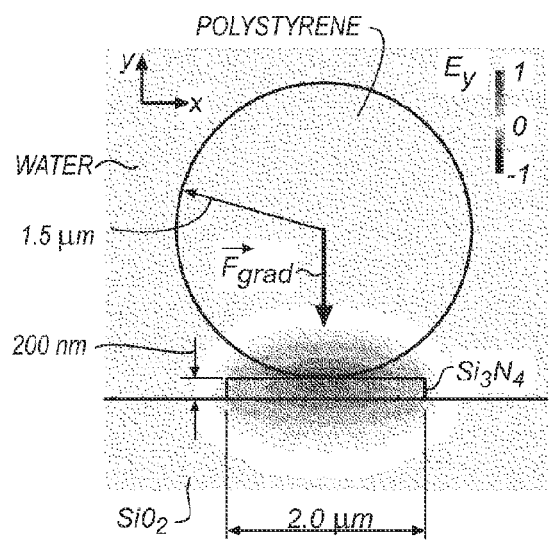
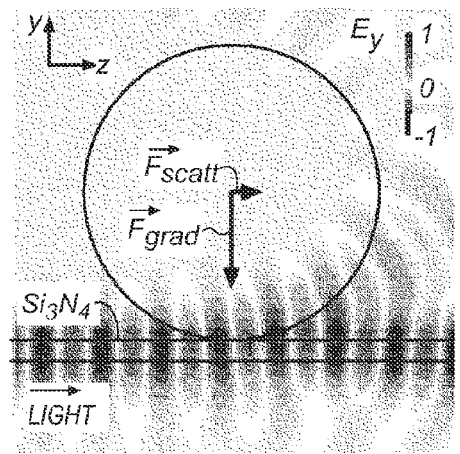
FIG. 17a     FIG. 17b

INTEGRATED OPTOFLUIDIC SYSTEM USING MICROSPHERES

CROSS-REFERENCE TO RELATED APPLICATIONS

This application is a U.S. National Phase patent application under 35 U.S.C. 371 of international application Serial No. PCT/US2010/036625, filed on May 28, 2010 which in turn claims priority to and the benefit of U.S. provisional patent application Ser. No. 61/182,868, entitled "Integrated Biosensor Using Microspheres," filed Jun. 1, 2009. The entire contents of the foregoing references are incorporated herein by reference.

STATEMENT REGARDING FEDERALLY SPONSORED RESEARCH OR DEVELOPMENT

The disclosed invention was made with government support under contract no. DGE-0654112 from the National Science Foundation. The government has rights in this invention.

1. TECHNICAL FIELD

The present invention relates generally to sensors integrated on planar substrates. The invention also relates to biosensors integrated on planar substrates. The invention further relates to optofluidic systems for trapping and transporting particles for analysis.

2. BACKGROUND OF THE INVENTION

Measurements of whispering gallery modes (WGMs) have been used successfully to detect the binding of single biomolecules (A. M. Armani, R. P. Kulkarni, S. E. Fraser, R. C. Flagan, and K. J. Vahala, "Label-free, single molecule detection with optical microcavities," Science 317(5839), 783-787 (2007)). WGM detection and measurement takes advantage of the resonant circulation of light around the circumference of a circular cavity to achieve such high sensitivities. However, coupling light into devices employing WGM detection and measurement is typically achieved using tapered optical fiber (F. Vollmer, D. Braun, A. Libchaber, M. Khoshsima, I. Teraoka, and S. Arnold, "Protein detection by optical shift of a resonant microcavity," Appl. Phys. Lett. 80(21), 4057-4059 (2002)) or a prism, and therefore a complete integrated system cannot be fabricated using standard photolithography techniques. There is a need in the art for label-free ultra-sensitive biosensors that can be miniaturized and integrated on a planar substrate and that can be fabricated using standard photolithography techniques.

Citation or identification of any reference in Section 2, or in any other section of this application, shall not be considered an admission that such reference is available as prior art to the present invention.

3. SUMMARY OF THE INVENTION

An integrated optofluidic system for trapping and transporting individual particles for analysis is provided. The integrated optofluidic system can comprise:
a planar substrate;
a microfluidic channel;
a sensor region or detection region fluidically connected to the microfluidic channel; and
a waveguide integrated with the microfluidic channel through which light is propagated.

In one embodiment, the integrated optofluidic system comprises the particles.

In another embodiment, the particles are microspheres.

In another embodiment, the microspheres are functionalized.

In another embodiment, the functionalized microspheres comprise an identifier binding ligand that will bind a decoder binding ligand such that the identification of an analyte can be elucidated.

In another embodiment, the waveguide optically traps particles out of the microfluidic channel.

In another embodiment, the particles are trapped, stopped or retained within the sensor region or detection region.

In another embodiment, the trapped particles continue to move in the direction of the light propagated through the waveguide.

In another embodiment, the integrated optofluidic system comprises a functionally coupled light source that produces light over an analytical wavelength range.

In another embodiment, the light source is a broadband light source and the analytical wavelength range is visible and near-infrared.

In another embodiment, the broadband light source produces visible and near-infrared wavelengths simultaneously.

In another embodiment, the light source is a supercontinuum light source.

In another embodiment, the integrated optofluidic system comprises a spectrometer.

In another embodiment, the integrated optofluidic system comprises a sample inlet port wherein the microfluidic channel is fluidically connected to the sample inlet port.

In another embodiment, the integrated optofluidic system comprises at least one sample handling well comprising a well inlet port and a well outlet port wherein:
the well inlet port and the well outlet port are fluidically connected to the sample handling well to allow fluid contact between the sample inlet port and the sample handling well; and
the well outlet port is fluidically connected to the microfluidic channel In another embodiment, the well inlet port and the well outlet port are the same port.

A method for trapping and transporting a particle for analysis is also provided. The method can comprise the steps of:
providing a waveguide;
optically trapping the particle with the waveguide;
exciting a resonant light scattering signature of the particle with a light source that produces light over an analytical wavelength range; and
measuring the resonant light scattering signature of the particle using the waveguide transmission.

In one embodiment, the light source is a broadband light source and the analytical wavelength range is visible and near-infrared.

In another embodiment, the broadband light source produces visible and near-infrared wavelengths simultaneously.

In another embodiment, the light source is a supercontinuum light source.

A method for trapping and transporting a particle for analysis is also provided. The method can comprise the steps of:
providing an integrated optofluidic system, wherein the system comprises:
a planar substrate;

a microfluidic channel;
a sensor region or detection region fluidically connected to the microfluidic channel; and
a waveguide integrated with the microfluidic channel through which light is propagated;
introducing the particle into the integrated optofluidic system;
optically trapping the particle in the sensor region or detector region with the waveguide;
exciting a resonant light scattering signature of the particle with a light source that produces light over an analytical wavelength range; and
measuring the resonant light scattering signature of the particle using the waveguide transmission.

In one embodiment, the method can comprise, after the measuring step, the step of releasing the particle by decreasing optical power or changing the wavelength of the light.

In another embodiment, the light source is a broadband light source and the analytical wavelength range is visible and near-infrared.

In another embodiment, the broadband light source produces visible and near-infrared wavelengths simultaneously.

In another embodiment, the light source is a supercontinuum light source.

In another embodiment, the resonant light scattering signature comprises whispering gallery mode (WGM) resonance.

In another embodiment, the steps of the method are repeated with a second particle.

A method for detecting binding of a target analyte is also provided. The method can comprise the steps of:
providing an integrated optofluidic system, wherein the system comprises:
a planar substrate;
a microfluidic channel;
a sensor region or detection region fluidically connected to the microfluidic channel and;
a waveguide integrated with the microfluidic channel through which light is propagated;
providing an identifiable functionalized microsphere that has an affinity for at least one target analyte;
introducing the functionalized microsphere into the integrated optofluidic system;
optically trapping the functionalized microsphere in the sensor region or detector region with the waveguide;
exciting a resonant light scattering signature of the functionalized microsphere with a light source that produces light over an analytical wavelength range, wherein the step comprises exciting the functionalized microsphere one or more times over a first analytical wavelength range to produce at least one reference resonant light scattering signature for the functionalized microsphere, the reference resonant light scattering signature uniquely identifying the functionalized microsphere; and
measuring the reference resonant light scattering signature of the functionalized microsphere using the waveguide transmission,
contacting the functionalized microsphere with a sample suspected of containing at least one analyte where, if the analyte is present in the sample, binding occurs between the functionalized microsphere and the at least one analyte;
scanning the contacted functionalized microsphere one or more times over a second analytical wavelength range to produce at least one binding resonant light scattering signature for the contacted functionalized microsphere, wherein:

the at least one reference resonant light scattering signature and the at least one second binding resonant light scattering signatures may be the same or different; and
the at least first and second analytical wavelength ranges may be the same or different;
measuring the binding resonant light scattering signature of the functionalized microsphere using the waveguide transmission,
detecting binding of the at least one analyte to the contacted functionalized microsphere by comparing the differences between the resonant light scattering signatures selected from the group consisting of: any of the at least one reference resonant light scattering signature and any of the at least one binding resonant light scattering signature; and
identifying one or more bound analytes on the basis of the at least one binding resonant light scattering signature.

In one embodiment, the at least one reference resonant light scattering signature and the at least one binding resonant light scattering signature is a WGM resonance.

In another embodiment, the light source is a broadband light source and the analytical wavelength range is visible and near-infrared.

In another embodiment, the broadband light source produces visible and near-infrared wavelengths simultaneously.

In another embodiment, the light source is a supercontinuum light source.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1. Design of the integrated optofluidic system.

FIG. 2. Photomicrograph of 3 μm microspheres and a waveguide in an embodiment of the integrated optofluidic system.

FIG. 3. Diagram showing a microsphere that is stopped and held stationary against an oxide interface. Resonances can be analyzed using optical transmission.

FIG. 4. Photomicrograph showing optical trapping and transport of polystyrene microspheres in an optofluidic channel. The glass (silicon dioxide cladding, "oxide cladding") interface provides a stop for trapped microspheres. The waveguide (horizontal line in center of photomicrograph) is in direct contact with fluid in the channel Oxide clad regions are indicated by arrows to the left and right of the unclad region.

FIG. 5. Diagram of an embodiment of the integrated optofluidic system. The silicon nitride waveguide can have high-index contrast and have low loss, which enables broadband transmission. The inset shows that in this embodiment, oxide n=1.46 and water n=1.33 for a waveguide 200 nm high and 2 μm wide.

FIG. 6. Diagram of an embodiment of the integrated optofluidic system showing a microfluidic channel in PDMS having a height of 30 μm and a width 300 μm.

FIG. 7. Diagram of an embodiment of the integrated optofluidic system. A microsphere (n=1.59) is introduced into a microfluidic channel of the integrated optofluidic system. In this embodiment, pressure driven flow is used to bring the microsphere to the waveguide.

FIG. 8. Diagram of an embodiment of the integrated optofluidic system. A microsphere is trapped by the evanescent field of the waveguide. Scattering forces transport the microsphere along the waveguide.

FIG. 9. Diagram of an embodiment of the integrated optofluidic system. Optical power is decreased and the microsphere resumes pressure drive flow.

FIG. 10. Consecutive photomicrographic images showing the trapping and transport of a 10 µm polystyrene microsphere by an integrated waveguide.

FIG. 11. Measurement of the transmission spectrum of an integrated waveguide trapping a polystyrene microsphere. The whispering gallery modes (WGM) resonances are clearly visible in the transmitted signal.

FIG. 12. Diagram showing a channel waveguide fabricated with standard lithography techniques.

FIG. 13. Diagram showing basic steps for fabricating an embodiment of the integrated optofluidic system using standard methods known in the art. The step for fabricating the nanophotonic component of the system, i.e., the silicon nitride waveguide, comprises fabricating the silicon nitride waveguide on the planar substrate using electron beam (ebeam) lithography. In this embodiment, the planar substrate comprises a layer of silica on a silicon substrate. The step for fabricating the microfluidic component of the system, i.e., the microfluidic channel in PDMS, comprises fabricating the microfluidic channel creating a resist on a silicon wafer using photolithography and creating the channel by pouring and baking PDMS on the silicon wafer-resist. The step of integrating the nanophotonics with the microfluidics comprises plasma cleaning the silicon nitride waveguide and the microfluidic channel in PDMS and performing contact alignment between the waveguide and the channel to create the integrated optofluidic system. A photograph of an embodiment of the integrated optofluidic system is shown at the bottom of the figure.

FIG. 14. Diagram showing steps for fabricating the photonics component of the integrated optofluidic system using standard methods known in the art.

FIG. 15. Diagram showing steps for fabricating the microfluidics component of the integrated optofluidic system using standard methods known in the art.

FIG. 16. Diagram showing a final step for fabricating the integrated optofluidic system, which can comprise aligning the photonic and microfluidic components of components of the system using a contact aligner according to standard methods known in the art.

FIGS. 17a-b. 3D simulation results for the electric field ($E_y$) profile of the quasi-TM mode at a wavelength of 850 nm in a silicon nitride waveguide. The optical forces on a dielectric microsphere can be decomposed into a transverse gradient force ($F_{grad}$), which traps the sphere to the waveguide surface and a longitudinal force ($F_{scatt}$), which propels it along the direction (z-axis) of light propagation.

FIG. 18. Spectra of the supercontinuum source (upper trace) and waveguide transmission (lower trace) showing efficient broadband coupling to the waveguide from 700 nm to 1400 nm The plots show efficient broadband coupling over ~700 nm range in the operation of the integrated optofluidic system. The plots show measured input (supercontinuum source, upper trace)/output (waveguide transmission, lower trace) power loss of ~10 dB.

FIG. 19. Photomicrograph of optical trapping and transport of 3 µm diameter polystyrene microspheres in a microfluidic channel using a supercontinuum broadband light source with ~10 mW of guided power.

FIG. 20. Waveguide transmission spectrum showing whispering gallery mode resonances of an optically trapped 18 µm diameter polystyrene microsphere with quality factors of ~2,000.

FIG. 21. Experimental (circles) free spectral range in microspheres of different diameters with theoretical curves (solid lines) for whispering gallery modes (WGMs) in spherical cavities.

5. DETAILED DESCRIPTION OF THE INVENTION

For clarity of disclosure, and not by way of limitation, the detailed description of the invention is divided into the subsections set forth below.

5.1 Integrated Optofluidic System

An integrated optofluidic system for trapping and transporting particles for analysis is provided. In one embodiment, the optofluidic system comprises:
a planar substrate;
a microfluidic channel; and
a waveguide, wherein the waveguide is integrated with the microfluidic channel The integrated optofluidic system can be a stand-alone device or integrated into any suitable microfluidics platform known in the art. In certain embodiments, the integrated optofluidic system can form a component on a chip (e.g., a "lab-on-a-chip") with other analysis capabilities. Particles and/or analytes that are analyzed by the integrated optofluidic system on the chip can be moved or pumped to other areas of the chip for further analysis or characterization.

The integrated optofluidic system can comprise at least one particle or sphere, termed herein a "microsphere." Any particle (spherical or substantially spherical) or microsphere known in the art can be used. In one embodiment, the microsphere can have a diameter that ranges from 1 um to 1 mm The diameter of the particle used can depend on the material properties of the particle and the wavelength of light used. The methods for analysis disclosed herein will work for any particle or sphere that supports whispering gallery modes, which can be determined by the ordinarily skilled practitioner. For polystyrene and glass particles, diameters can generally be a few microns and larger. Silicon microspheres can be smaller and still support these WGMs, (e.g., in the range of 100s of nm, 100 nm-1 mm, etc.). There is no upper size limit for particles for use in the integrated optofluidic system and methods of the invention.

Particles can be separate components that are introduced into the integrated optofluidic system or they can be comprised in the system. In a specific embodiment, particles are injected into the microfluidic channel using pressure driven flow according to methods known in the art. Any other pumping or fluid flow method known in the art can be used to introduce or move particles within the microfluidic channel.

The integrated optofluidic system can comprise a plurality of particles or microspheres. In another embodiment, a plurality of particles or microspheres can be added or introduced into the integrated optofluidic system.

The microsphere in the integrated optofluidic system can act as a cavity, allowing light to circulate many thousands of times around the circumference of the microsphere. Sensitive measurements on molecules (including, but not limited to biomolecules) can be accomplished by monitoring changes in resonances, e.g., high quality factor whispering gallery modes (WGMs), that propagate around the circumference of the microsphere.

The microsphere can comprise, or consist of, a material such as silica, silicon, silicon nitride, silicon oxinitride, polystyrene, polyethylene, or any other glass or polymer known in the art.

The microspheres can be functionalized or non-functionalized.

In a specific embodiment, polystyrene microspheres are used. Polystyrene microspheres of various diameters are known in the art and commercially available (e.g., Duke Scientific). They can be prepared according to methods known in the art, e.g., in a 10 mM phosphate buffer solution, and injected into the microfluidic channel using pressure driven flow.

The integrated optofluidic system comprises a planar substrate. Any planar substrate or "chip" substrate known in the art can be used, such as quartz, silica, silicon or gallium arsenide. In a preferred embodiment, the planar substrate is a silicon wafer.

The integrated optofluidic system comprises on one or more microfluidic channels integrated on the planar substrate for transporting and positioning microspheres. Any type of microfluidic channel known in the art can be used. The microfluidic channels can be fluidically connected to a sensor region (also referred to herein as a "sensing region" or a "detection region") and can carry or direct microspheres to the sensor region, where the microspheres can be, in certain embodiments, trapped, stopped or retained. In a preferred embodiment, the microfluidic channel is a channel that is formed in a layer of polydimethylsiloxane (PDMS) deposited on the planar substrate. In other embodiments, the microfluidic channel can be formed of silica (glass) or other materials for microfluidic channels known in the art. The integrated optofluidic system can comprise one or more integrated waveguides. The integrated waveguide can be a straight waveguide, a ring resonator, another type of cavity or other plasmonics structures known in the art. The integrated waveguide(s) optically trap a particle or microsphere out of the flow of the microfluidic channel and can, in certain embodiments, stop or retain it in the sensor (or detection) region, or cause it to move along the direction of light in the waveguide. The integrated optofluidic system can also comprise sensor (or "sensing" or "detection") region in which particles/microspheres are analyzed or characterized. Particles may be optionally stopped, trapped or retained in the sensor region. A particle can also be measured or analyzed while it not stopped, but as it continues to move or be pushed along the direction of light.

The microsphere can act as a cavity, allowing light to circulate many thousands of times around the circumference of the microsphere. In certain embodiments, light transmitted through the waveguide can be used to measure these resonances. Analysis can be performed on a particle or microsphere in the sensor (or detection) region using the integrated waveguide(s). Light transmitted through the waveguide(s) is used to measure resonances e.g., high quality factor whispering gallery modes (WGMs), that propagate around the circumference of the microsphere. Resonance measurements can be used to monitor the binding of individual molecules (e.g., biomolecules).

In one embodiment, the waveguide is a silicon nitride ($Si_3N_4$) waveguide. In other embodiments, the waveguide can be made of any waveguide materials known in the art such as silicon, doped glass, polymers, SU8, etc. The optimal dimensions of the waveguide and microfluidic channel are application-dependent and hence various embodiments can use different sizes for the various structures. The ordinarily skilled practitioner, using art-known methods, can determine these dimensions for the waveguide and microfluidic channel In one embodiment of the device, the waveguide transports the particles along the direction of light propagation until the particles reach a sensor region. In one embodiment, the sensor region is a physical barrier or interface (e.g., glass) at which the particles are stopped, trapped or retained.

In other embodiments, the particles (e.g., microspheres) are not stopped, trapped or retained to analyze them. The particles can be analyzed or measured at any location on the waveguide without stopping them.

In another embodiment of the device, the waveguides transport the particles to other types of sensor regions, e.g., to sensor regions that comprise electrodes that perform electrochemical measurements. As discussed herein, either changing the power or wavelength of the light in the waveguides can control the speed at which particles are moved by the waveguides.

In a specific embodiment, the sensor region comprises an oxide interface. In other embodiments, the sensor region can comprise any interface or surface known in the art that can retain particles or microspheres.

In other embodiments, the sensor region does not stop or retain particles and/or does not comprise a surface or interface that retains particles. The methods of optical trapping disclosed herein can hold or push particles along the direction of light. Either changing the power or the wavelength of the light can control the speed at which a particle moves.

In other embodiment, the sensor region can comprise an art-known sensor such as an electrode, photodetector, temperature sensor, microcantilever or MEMS device or can be coupled to such a sensor.

The light transmitted through the waveguide(s) can be used to monitor the binding of individual molecules. In a specific embodiment, a biomolecule is analyzed or monitored. The biomolecule can be any biomolecule known in the art, i.e., any organic molecule that is produced by a living organism, including, but not limited to, large polymeric molecules such as proteins, polysaccharides, and nucleic acids as well as small molecules such as primary metabolites, secondary metabolites, and natural products. The integrated optofluidic system can thus serve, in certain embodiments, as an on-chip, label-free biosensor for performing sensitive measurements on biomolecules.

In the integrated optofluidic system provided herein, a light source, e.g., a broadband light source, can be used with one or more waveguides to optically trap one or more microspheres in the sensor region. In a specific embodiment, the integrated optofluidic system comprises a light source functionally coupled to the waveguides. Methods for coupling light sources to waveguides are known in the art.

In a specific embodiment, supercontinuum generated light is used as the light source for integrated waveguides. Supercontinuum light sources are known in the art and are commercially available (e.g., Fianium SC450). A supercontinuum light source emits light over a large range of wavelengths (500 nm-1.5 microns). The supercontinuum light source is preferred, and offers advantages over, art-known sources such as fixed wavelength lasers or tunable lasers, when used to measure particle resonances. However, in less preferred embodiments, fixed wavelength lasers or tunable lasers could also be used as the light source.

A supercontinuum light source also has advantages over using other types of broadband sources, e.g., LEDs or mercury lamps. It has higher power but it also has high spatial coherence, which is used to focus the light down so that it can be coupled into waveguides efficiently. Other broadband light sources (e.g., light bulbs) lack this spatial coherence. Hence coupling light into waveguides using a non-supercontinuum light source can be very inefficient (i.e., much light is lost in the coupling process). Hence, a supercontinuum source is a preferred source for use with the integrated optofluidic system, and even more preferred in applications that involve on-chip analysis.

The optical trapping of the microsphere can serve two purposes: to precisely position the microsphere next to the waveguide as well as to couple light into the microsphere. Light can be coupled efficiently into WGMs of microspheres using the evanescent field from the integrated waveguides. The amount of light coupled to waveguides can be altered by waveguide dimension optimization using methods known in the art.

In a specific embodiment of the integrated optofluidic sensor, light from a high-power broadband source can be coupled into a single mode fiber and then into a sensor, e.g., a photonic chip (commercially available and/or known in the art), using a tapered lens fiber. The high-power broadband source can be any known in the art, e.g., a 4 W fiber pumped supercontinuum source (Fianium SC450), which provides a wavelength range of 475 nm-1500 nm with spectral density of ~2 mW/nm The waveguide output is collected with a high NA microscope objective and measured with a spectrometer (e.g., Ocean Optics). From recorded output power measurements and estimates for the waveguide losses and output coupling efficiency, it is estimated that the guided power within the silicon nitride waveguides is no greater than 5 mW.

A spectrometer (known in the art and/or commercially available) can be used to analyze the spectrum of the light transmitted through the waveguide from the sensor region. The WGM resonances of the trapped microspheres will be clearly visible. Since the light propagates many times around the circumference of the microspheres, the interaction length between the light and the surrounding fluid is greatly increased. Therefore, any changes in the properties (such as absorption or refractive index) will result in a change in shape of these resonances. The integrated optofluidic system thus provides a sensitive device for measuring absorption characteristics of bulk fluids in the wavelength range spanning the visible to the mid-infrared.

Several broadband particle characterization methods can be used in conjunction with analysis of WGM resonances, including fluorescence and scattering spectroscopy (P. Li, K. B. Shi, and Z. W. Liu, "Manipulation and spectroscopy of a single particle by use of white-light optical tweezers," Opt. Lett. 30(2), 156-158 (2005)) as well as coherent anti-stokes raman spectroscopy (K. B. Shi, P. Li, and Z. W. Liu, "Broadband coherent anti-stokes raman scattering spectroscopy in supercontinuum optical trap," Appl. Phys. Lett. 90(14), 3 (2007)).

Other components that can be optionally included as components of the integrated microfluidic system can be a laser source or a power meter.

In another embodiment, the integrated optofluidic system can be positioned completely on-chip. The embodiment of the device shown in FIG. 1 relies on one or more microfluidic channels and on optical trapping to transport microspheres for individual analysis. After centimeter scale transport within a microfluidic channel, the microspheres are trapped by the art-known gradient forces generated by the decay of the evanescent field of the waveguide. In addition to this lateral gradient force, there is an art-known axial force owing to scattering and absorption that propels the particles along the direction of light propagation (B. S. Schmidt, A. H. J. Yang, D. Erickson, and M. Lipson, "Optofluidic trapping and transport on solid core waveguides within a microfluidic device," Optics Express 15(22), 14322-14334 (2007)). This optical trapping and transport is used for the nanoscale positioning necessary to excite the microsphere resonances. By using a broadband light source, the microspheres can be trapped and many WGM resonances can be excited through the visible and near-infrared wavelengths simultaneously. After the resonances are measured using the waveguide transmission, the microsphere can be freed by decreasing the optical power and the process repeated with a different microsphere.

FIG. 2 shows 3 µm microspheres and a waveguide in an embodiment of the integrated optofluidic system.

FIG. 3 shows a microsphere stopped and held stationary against a sensor region that is an oxide interface. Resonances can be analyzed in this sensor region using optical transmission. By contrast, in prior art devices, an optical fiber is precisely positioned next to a fixed sphere to excite WGMs, which prevents them from being used for integrated lab-on-a-chip applications.

FIG. 4 is a photomicrograph showing optical trapping and transport of polystyrene microspheres in an optofluidic channel (i.e., a channel comprising a microfluidic channel and a waveguide). The glass (oxide clad) interface (sensor region) provides a stop for trapped microspheres. The waveguide (horizontal line in center of photomicrograph) is in direct contact with fluid in the microfluidic channel. Oxide clad regions are indicated by arrows to the left and right of the unclad region.

FIG. 5 is a diagram of a specific embodiment of the integrated optofluidic system that comprises one or more silicon nitride ($Si_3N_4$) waveguides integrated with one or more microfluidic channel in polydimethylsiloxane (PDMS). The waveguides have high-index contrast and have low loss, which enables broadband transmission. The inset shows that oxide n=1.46 and water n=1.33 for a waveguide 200 nm high and 2 µm wide. The high refractive index of silicon nitride (n=2.0) compared to that of silicon oxide (n=1.46) and water (n=1.33) leads to a highly confined optical mode and a strong evanescent field gradient that enables efficient trapping of particles.

Water and other fluids can be used in the integrated optofluidic system, e.g., any of the many suitable aqueous buffers (e.g., phosphate buffered saline) known in the art for use with biomolecules, cells, cell extracts, and other biological materials.

FIG. 6 shows the design of a microfluidic channel in PDMS. In this exemplary embodiment, the height of the microfluidic channel is 30 µm and the width is 300 µm. Other suitable dimensions for microfluidic channels are known in the art or can be readily determined by an ordinarily skilled practitioner.

FIG. 7 shows a polystyrene microsphere (n=1.59) introduced into a microfluidic channel. In this embodiment of the integrated optofluidic system, pressure driven flow is used to bring microspheres to the waveguide. Other pumping or fluidic flow systems suitable for moving particles are known in the art and can be employed in the integrated optofluidic system.

Figure 1:
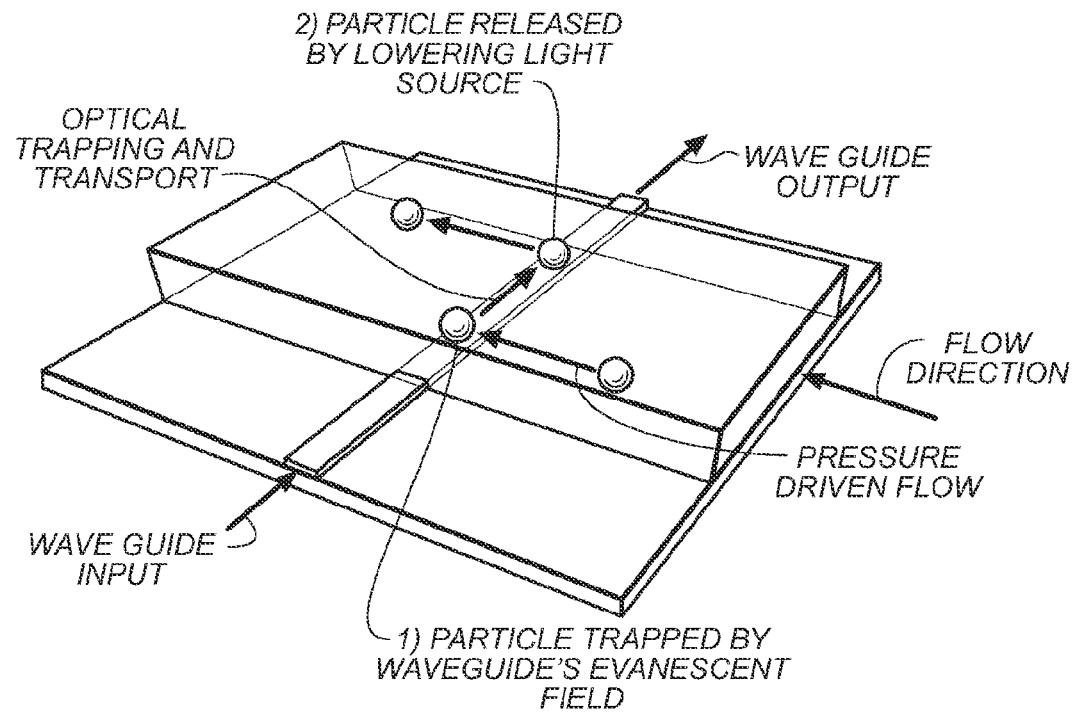
Figure 2:
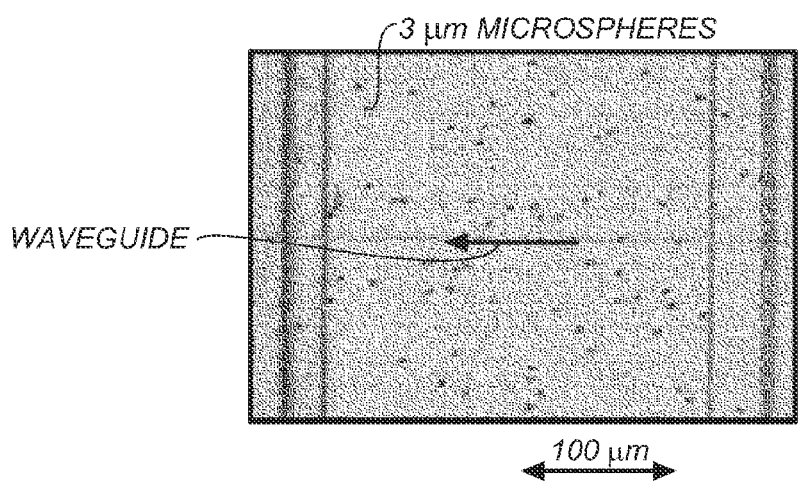
Figure 3:
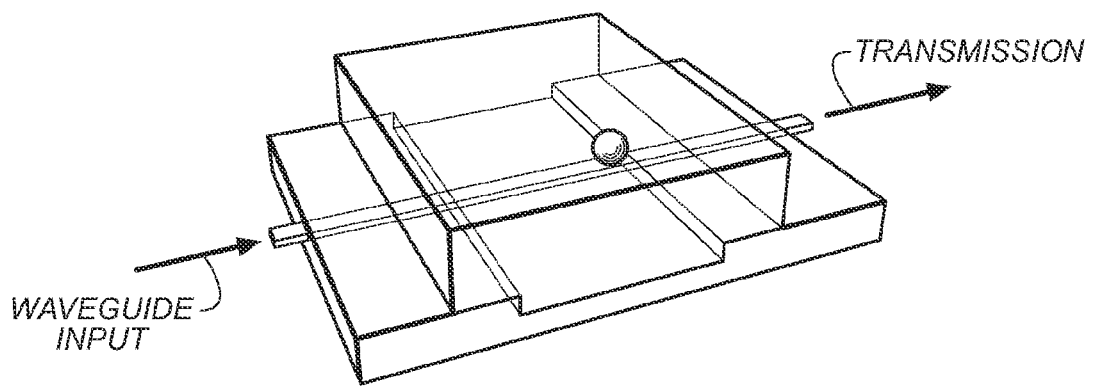
FIG. 3 shows a microsphere stopped and held stationary against the sensor region, which in this embodiment, is an oxide interface. Resonances can be analyzed in the sensor region using optical transmission.
Figure 4:
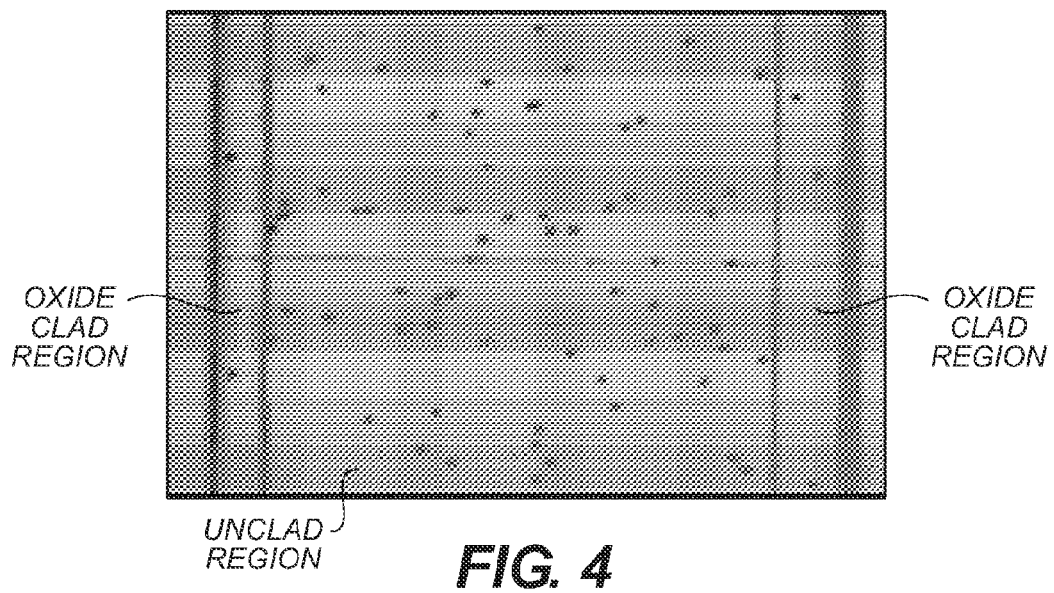
Figure 5:
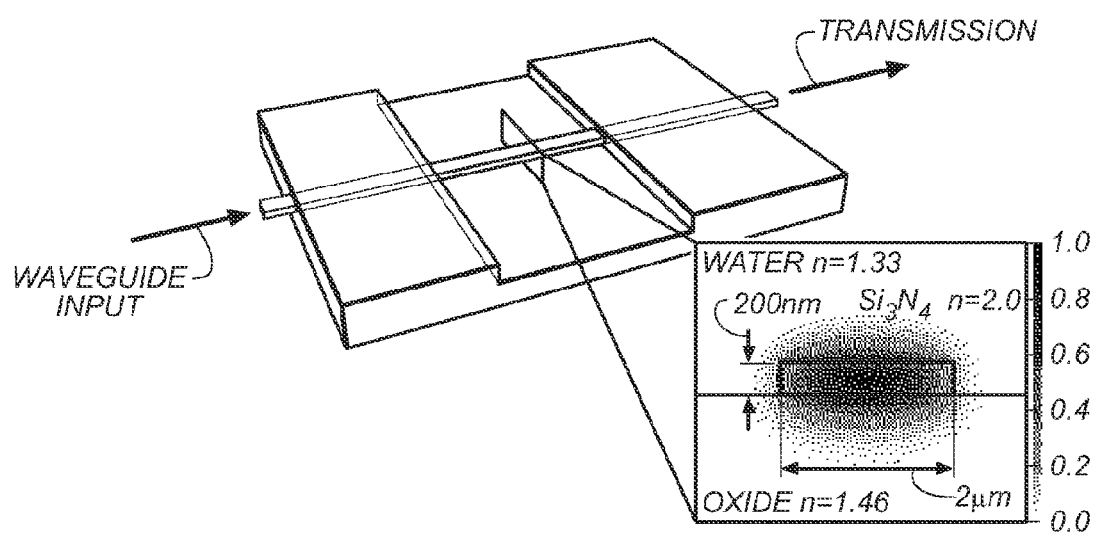
Figure 6:
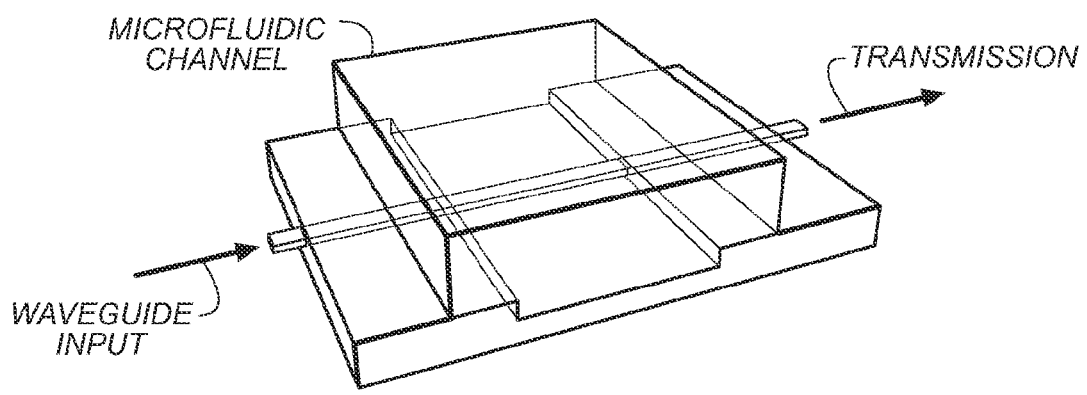
Figure 7:
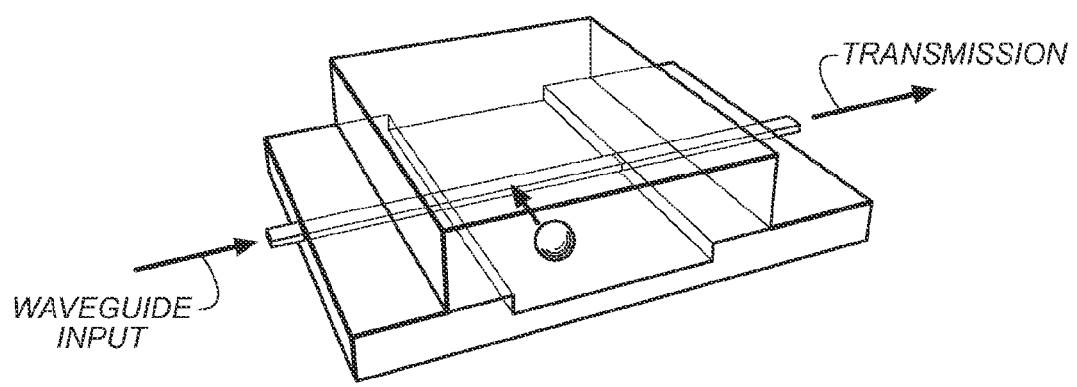
Figure 8:
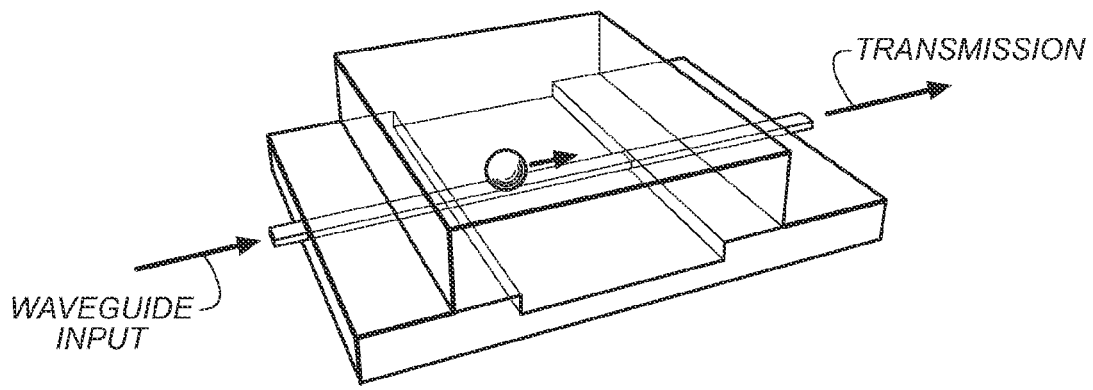
FIG. 8 shows a microsphere trapped by the evanescent field of the waveguide. Scattering forces transport microspheres along the waveguide.
Figure 9:
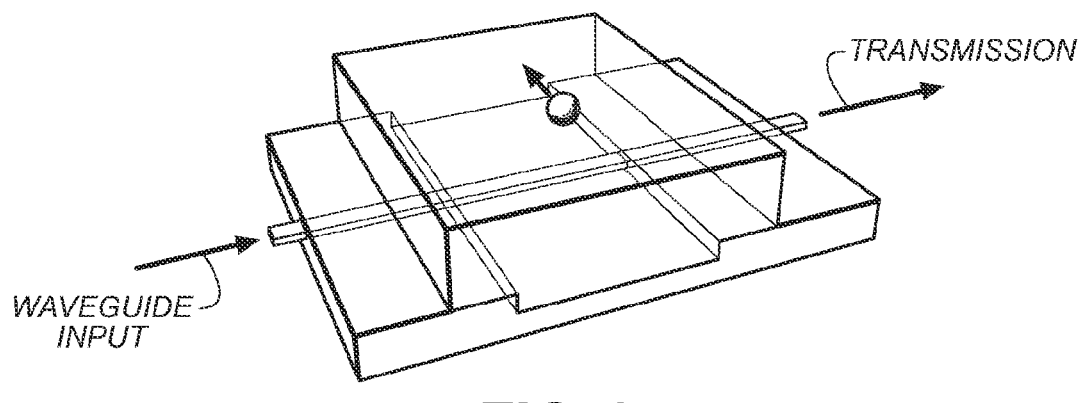
FIG. 9 shows a point at which the optical power has decreased and the microsphere has resumed pressure drive flow.
Figure 10:
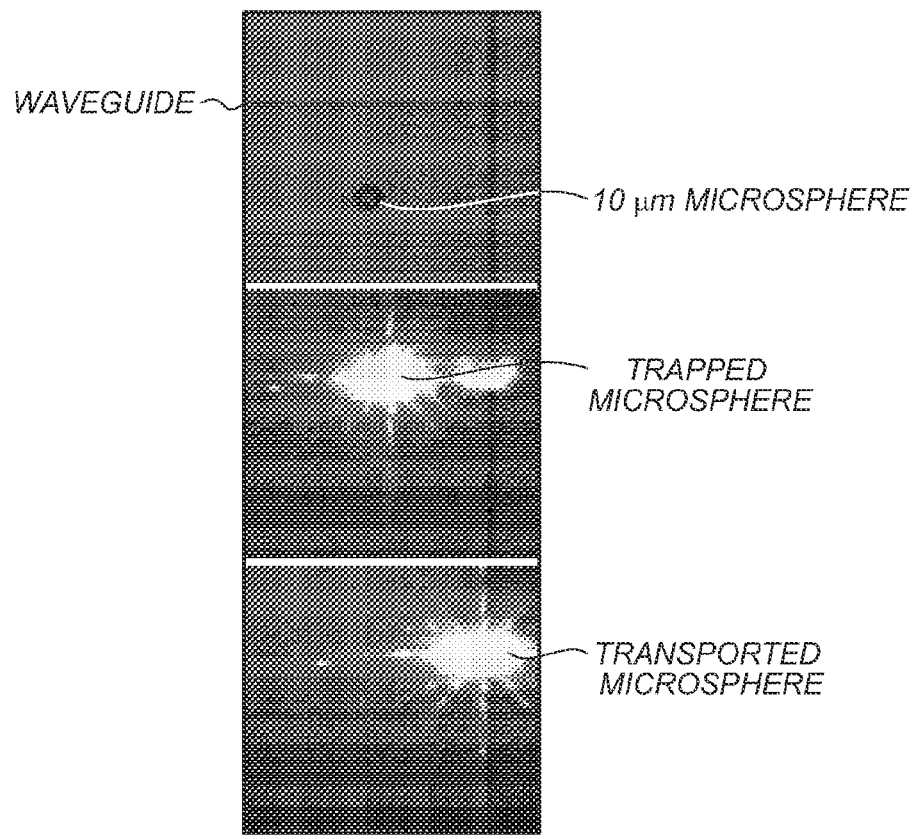

The light that traps microspheres also excites their WGM resonances. FIG. 10 shows a sequence of microscope images showing a 10 μm diameter polystyrene microsphere that is flowing in a microfluidic channel, then trapped and transported along the waveguide.

Figure 11:
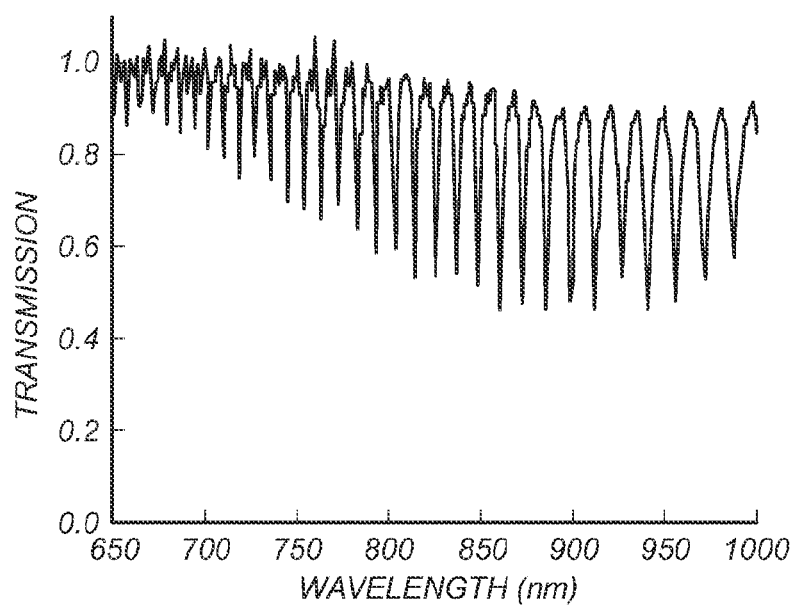

FIG. 11 shows the transmission spectrum of a waveguide while trapping a polystyrene microsphere. The dips in the transmission clearly correspond to the resonant wavelengths that are coupled into the microsphere.

This demonstration of efficient coupling of light into WGM resonances using channel waveguides demonstrates that the integrated optofluidic system can be used with microspheres as a biosensor by measuring changes in the resonance shape or position when biomolecules bind to the surfaces of the microspheres. This platform solves the integration challenges of current, art-known WGM-based sensors and can be used to realize ultra-sensitive biosensors for lab-on-a-chip applications.

Besides using the WGM resonances of dielectric particles, the integrated optofluidic system can trap metallic particles such as gold or silver. Metallic particles have surface plasmon resonances that are also sensitive to binding events on their surface and therefore can be used in the integrated optofluidic device and/or form the basis for a biosensor.

Any metallic particle known in the art can be used with the integrated optofluidic system. Other particles suitable for use in the integrated optofluidic system and for optical trapping methods can include, but are not limited to silicon particles, magnetic, dyed, or fluorescent microspheres, or microspheres with quantum dots incorporated in them.

5.2 Functionalized Microspheres

The integrated optofluidic system can be used to analyze single particles for various applications. In one embodiment, the system can be used as a biosensor in which the shifts in the resonance wavelength are monitored as biomolecules bind to the surface of microspheres. By using functionalized microspheres, the binding of specific biomolecules can be detected with high sensitivity.

Functionalized microspheres that can be used in the integrated optofluidic system can include, but are not limited to microspheres conjugated with proteins such as biotin or streptavidin, microspheres conjugated with antibodies, and microspheres functionalized with amino, carboxylate, carboxy-sulfate, sulfate and/or hydroxylate groups.

In some embodiments, microspheres may comprise identifier binding ligands for use in certain decoding or analytic systems. As referred to herein, an identifier binding ligand (IBL) means a compound that specifically binds a corresponding decoder binding ligand (DBL) to facilitate the elucidation of the identity of a biomolecule. That is, the IBL and the corresponding DBL form a binding partner pair. "Specifically bind" means herein that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$-$10^{-6}$ M$^{-1}$, with less than about $10^{-5}$ to $10^{-9}$ M$^{-1}$ being preferred and less than about $10^{-7}$-$10^{-9}$ M$^{-1}$ being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion-metal ion ligands or chelators pairs are also useful. Antigen-antibody pairs, enzymes and substrates or inhibitors, other protein-protein interacting pairs, receptor-ligands, complementary nucleic acids, and carbohydrates and their binding partners are also suitable binding pairs. Nucleic acid-nucleic acid binding proteins pairs are also useful. Similarly, as is generally described in U.S. Pat. Nos. 5,270,163, 5,475,096, 5,567,588, 5,595,877, 5,637,459, 5,683,867, 5,705,337, and related patents, nucleic acid "aptamers" can be developed for binding to virtually any target; such an aptamer-target pair can be used as the IBL-DBL pair. Similarly, there is a wide body of literature relating to the development of binding pairs based on combinatorial chemistry methods.

In a specific embodiment, the IBL-DBL pair comprises substantially complementary single-stranded nucleic acids. In this embodiment, the binding ligands can be referred to as "identifier probes" and "decoder probes". Generally, the identifier and decoder probes range from about 4 base pairs in length to about 1000 base pairs in length, with from about 6 to about 100 base pairs in length being preferred, and from about 8 to about 40 base pairs in length being particularly preferred. The probes are preferably long enough to be specific, i.e. to distinguish between different IBL-DBL pairs, yet short enough to allow dissociation (if necessary, under suitable experimental conditions) and efficient hybridization.

5.3 Target Analytes

Integrated optofluidic systems are provided that can be used to detect or quantify a target analyte (i.e., an analyte of interest). The integrated optofluidic systems can comprise one or more wells for sample manipulation, waste or reagents; microchannels to and between these wells to control fluid movement; on-chip pumps such as electroosmotic, electrohydrodynamic, or electrokinetic pumps; valves; and detection systems or sensors. These features are art known components of microfluidic chips or platforms. The integrated optofluidic system can be configured to manipulate one or multiple samples or analytes.

The integrated optofluidic system can be used to detect a target analyte in a sample. By "target analyte" or "analyte" or grammatical equivalents herein is meant any molecule, compound or particle to be detected. In one embodiment, a target analyte binds to a binding ligand or other functional molecule on a microsphere.

A large number of art-known analytes can be detected using the integrated optofluidic system and methods based thereon. Such analytes include, but are not limited to organic and inorganic molecules, including biomolecules. The analyte may be an environmental pollutant (e.g., pesticides, insecticides, toxins); a chemical (e.g., solvents, polymers, organic materials); therapeutic molecules (e.g., therapeutic and abused drugs, antibiotics); and biomolecules, including but not limited to nucleic acids, hormones, cytokines, proteins (e.g., enzymes, antibodies, antigens, growth factors, cytokines), lipids, carbohydrates, cellular membrane antigens and receptors (e.g., neural, hormonal, nutrient, or cell surface receptors, or their ligands).

In a specific embodiment, the target analyte is a nucleic acid. By "nucleic acid" or "oligonucleotide" or grammatical equivalents herein means at least two nucleotides covalently linked together. A nucleic acid will generally contain phosphodiester bonds, although in some cases, as outlined below, nucleic acid analogs are included that may have alternate backbones, comprising, for example, phosphoramide, phosphorothioate, phosphorodithioate, O-methylphophoroamidite linkages, and peptide nucleic acid backbones and linkages. Other analog nucleic acids include those with positive backbones; non-ionic backbones and non-ribose backbones. Nucleic acids containing one or more carbocyclic sugars and peptide nucleic acids are also included within the definition of nucleic acids. As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside. In a preferred embodiment, methods for detecting target nucleic acids are provided. By "target nucleic acid" or "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. In some embodiments, it may be desirable to fragment or cleave the sample nucleic acid into fragments of 20 to 10,000 base pairs, with fragments of roughly 500 base pairs being preferred in some embodiments. For hybridization purposes, smaller fragments are generally preferred. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others.

Probes (including primers) can be made to hybridize to target sequences to determine the presence or absence of the target sequence in a sample.

5.4 Design and Fabrication of Integrated Optofluidic System

The integrated optofluidic system can be fabricated using standard lithography methods known in the art.

Figure 12:
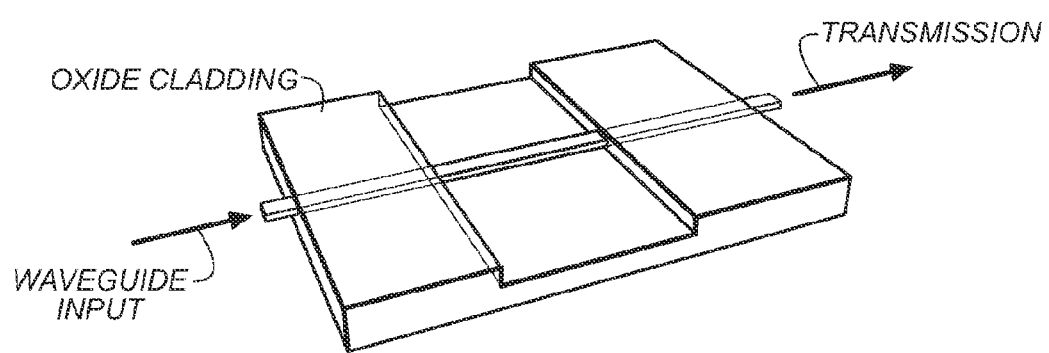

FIG. 12 is a diagram showing how channel waveguides can be fabricated using standard lithography techniques.

Figure 13:
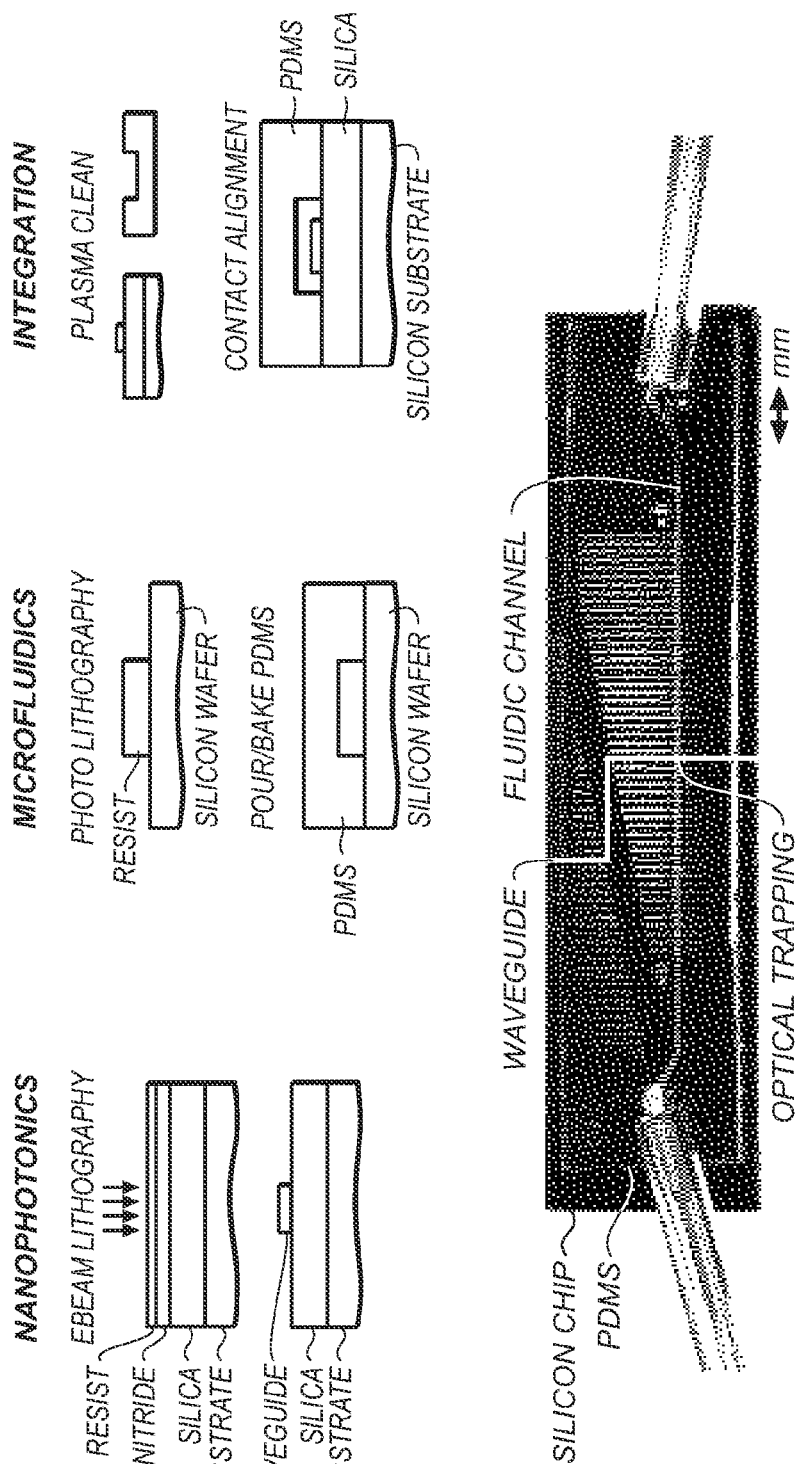

FIG. 13 is a summary of one approach for fabricating an integrated optofluidic system using standard methods known in the art. The step for fabricating the nanophotonic component of the system, i.e., the silicon nitride waveguide, comprises fabricating the silicon nitride waveguide on the planar substrate using electron beam (ebeam) lithography. In this embodiment, the planar substrate comprises a layer of silica on a silicon substrate. The step for fabricating the microfluidic component of the system, i.e., the microfluidic channel in PDMS, comprises fabricating the microfluidic channel creating a resist on a silicon wafer using photolithography and creating the channel by pouring and baking PDMS on the silicon wafer-resist. The step of integrating the nanophotonics with the microfluidics comprises plasma cleaning the silicon nitride waveguide and the microfluidic channel in PDMS and performing contact alignment between the waveguide and the channel to create the integrated optofluidic system. An embodiment of the integrated optofluidic system is shown at the bottom of the figure.

Figure 14:
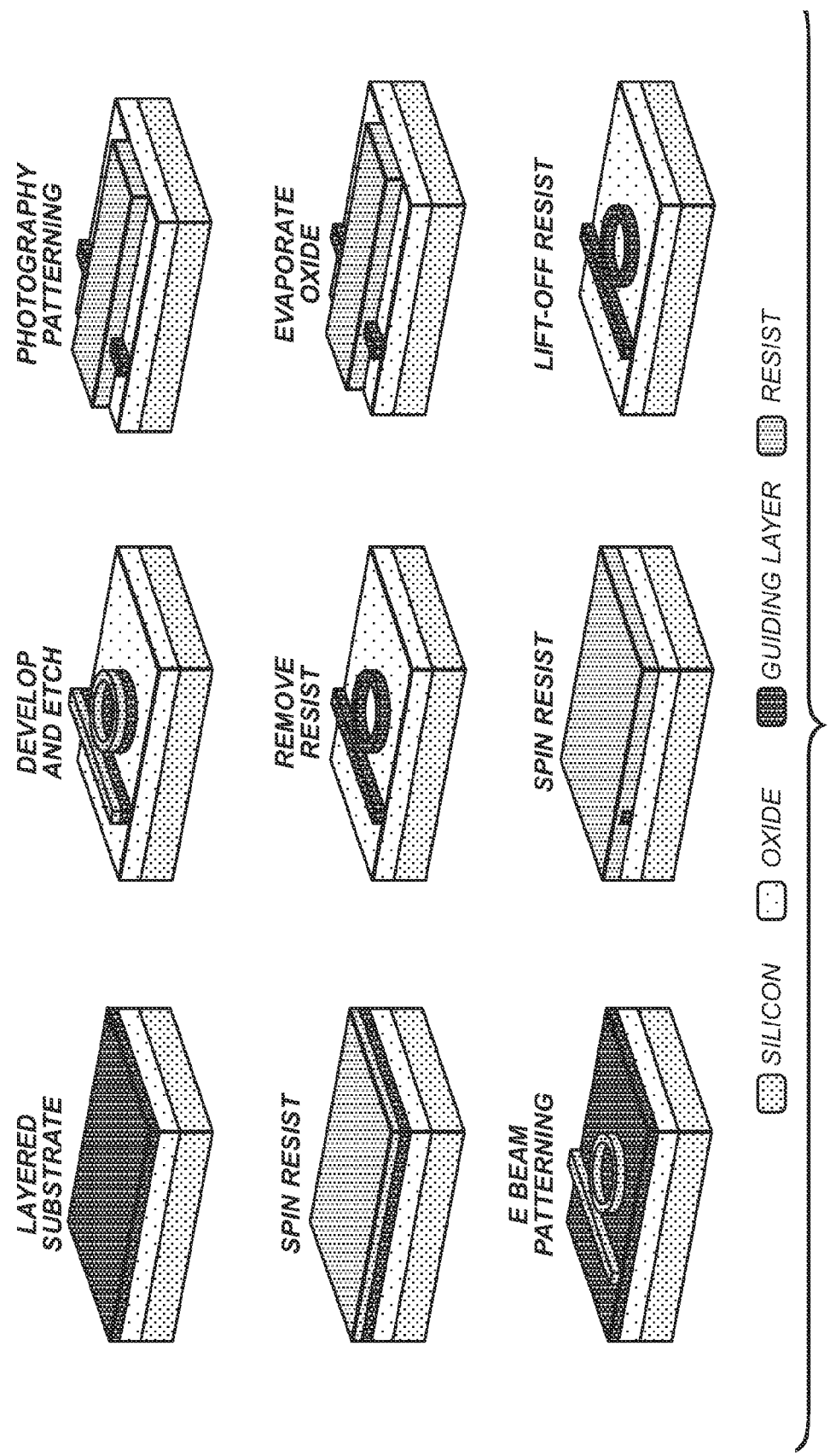

FIG. 14 is a summary of the general steps for fabricating the photonic component(s) of the integrated optofluidic system using standard methods known in the art.

Figure 15:
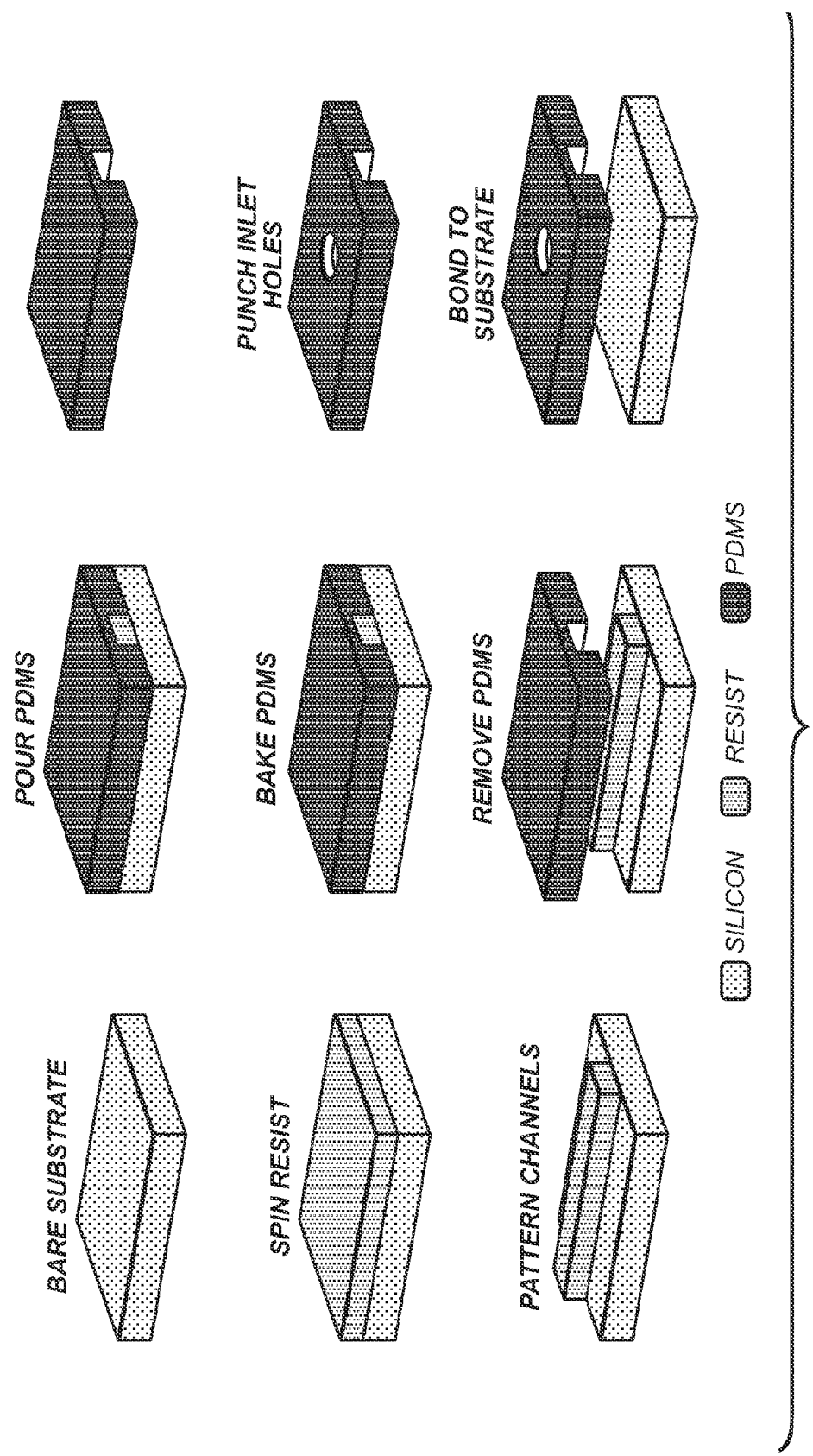

FIG. 15 is a summary of the general steps for fabricating the microfluidic components of the integrated optofluidic system using standard methods known in the art.

FIG. 16 shows a final step for fabricating the integrated optofluidic system, which can comprise aligning the photonic and microfluidic components of components of the system using a contact aligner according to standard methods known in the art.

In a specific embodiment, the integrated optofluidic system can be fabricated using methods known in the art, starting with a planar substrate that is a silicon wafer, on top of which 5 µm of thermal oxide is grown (A. Gondarenko, J. S. Levy, and M. Lipson, "High confinement micron-scale silicon nitride high q ring resonator," Opt. Express 17(14), 11366-11370 (2009)). A 200 nm device layer of silicon nitride is then deposited using low pressure chemical vapor deposition. Waveguides with 2 µm width are patterned using electron beam lithography followed by inductively coupled plasma etching. Microfluidic channels are made using standard soft lithography processes. A 30 µm tall by 300 µm wide channel is patterned with SU8 on top of a separate silicon wafer to act as a mold for the microfluidic channels. PDMS is poured over the mold, baked for several hours, and then inlet holes are punched into the PDMS. The microfluidic channels are then aligned on top of the waveguides.

5.5 Methods for Detecting Target Analytes Using the Integrated Optofluidic System Methods for detecting target analytes using the integrated optofluidic system are also provided.

In one embodiment, a method for trapping and transporting particles for analysis is provided. The method can comprise the steps of:

providing an integrated optofluidic system as disclosed herein, wherein the system comprises a planar substrate, a microfluidic channel, a sensor region or detection region fluidically connected to the microfluidic channel, and a waveguide integrated with the microfluidic channel through which light is propagated;

trapping the particle in the sensor region or detector region with the waveguide;

exciting a resonant light scattering signature of the particle with a light source that produces light over an analytical wavelength range; and measuring the resonant light scattering signature of the particle using the waveguide transmission.

The method can further comprise, after the measuring step, releasing or freeing the particle by decreasing optical power or changing the wavelength of the light.

Unlike prior art analytic methods of optical trapping, this method can employ same light source for both trapping the particle and analyzing it. The same light source can also be used to move the particles to other on-chip areas for further analysis.

In another embodiment, the light source is a broadband light source and the analytical wavelength range is visible and near-infrared.

In a preferred embodiment, the resonant light scattering signature comprises whispering gallery mode (WGM) resonance.

In another embodiment, the steps of the method are repeated with a second (different) particle. Trapping, moving and releasing particles for analysis can be controlled by changing the power or wavelength of the light.

In another embodiment, the broadband light source produces visible and near-infrared wavelengths simultaneously.

In a specific embodiment, the particle is an identifiable functionalized microsphere that has an affinity for at least one target analyte. According to this embodiment, the step of exciting a resonant light scattering signature can comprise exciting the functionalized microsphere one or more times over a first analytical wavelength range to produce at least one reference resonant light scattering signature for the functionalized microsphere, the reference resonant light scattering signature uniquely identifying the functionalized microsphere. The method can further comprise contacting the functionalized microsphere with a sample suspected of containing at least one analyte under conditions in which, if the analyte is present in the sample, binding occurs between the functionalized microsphere and the at least one analyte and scanning the contacted functionalized microsphere one or more times over a second analytical wavelength range to produce at least one binding resonant light scattering signature for the contacted functionalized microsphere. The at least one reference resonant light scattering signature and the at least one second binding resonant light scattering signatures may be the same or different. The at least first and second analytical wavelength ranges may be the same or different.

The method can further comprise detecting the binding of the at least one analyte to the contacted functionalized microsphere. This can be accomplished by comparing the differences between the resonant light scattering signatures selected from the group consisting of any of the at least one reference resonant light scattering signature and any of the at least one binding resonant light scattering signature.

The method can further comprise identifying one or more bound analytes on the basis of the at least one binding resonant light scattering signature. In a specific embodiment, the at least one reference resonant light scattering signature and the at least one binding resonant light scattering signature is a WGM resonance.

The following examples are offered by way of illustration and not by way of limitation.

6. EXAMPLES 6.1 Example 1: On-Chip Supercontinuum Optical Trapping and Resonance Excitation of Microspheres This example demonstrates the simultaneous optical manipulation and analysis of microscale particles in a microfluidic platform. Whispering gallery modes (WGMs) in dielectric microspheres were excited using the evanescent field from a silicon nitride waveguide. A supercontinuum source was used to both trap the microspheres to the surface of the waveguide and excite their resonant modes. All measurements were in-plane thus providing an integrated optofluidic platform for lab-on-a-chip biosensing applications.

6.1.1 Introduction

Optical trapping has been demonstrated as a critical tool for the manipulation of microscale particles for many biological applications (A. Ashkin and J. M. Dziedzic, "Optical trapping and manipulation of viruses and bacteria," Science 235(4795), 1517-1520 (1987)). Furthermore, it has been shown that the combination of optical trapping forces with the precise control provided by microfluidics can produce optofluidic lab-on-chips with increased functionalities (D. Psaltis, S. R. Quake, and C. H. Yang, "Developing optofluidic technology through the fusion of microfluidics and optics," Nature 442(7101), 381-386 (2006)). Recent progress in this area has included various devices to generate the near field intensity gradients required to achieve optical trapping (B. S. Schmidt, A. H. J. Yang, D. Erickson, and M. Lipson, "Optofluidic trapping and transport on solid core waveguides within a microfluidic device," Optics Express 15(22), 14322-14334 (2007); A .H. J. Yang, S. D. Moore, B. S. Schmidt, M. Klug, M. Lipson, and D. Erickson, "Optical manipulation of nanoparticles and biomolecules in sub-wavelength slot waveguides," Nature 457(7225), 71-75 (2009); S. Kuhn, P. Measor, E. J. Lunt, B. S. Phillips, D. W. Deamer, A. R. Hawkins, and H. Schmidt, "Loss-based optical trap for on-chip particle analysis," Lab Chip 9(15), 2212-2216 (2009); X. Y. Miao, B. K. Wilson, S. H. Pun, and L. Y. Lin, "Optical manipulation of micron/submicron sized particles and biomolecules through plasmonics," Optics Express 16(18), 13517-13525 (2008)). In most realizations of optical manipulation, a single narrowband light source is utilized. This example demonstrates the use of broadband light to generate optical forces on an integrated structure as a tool for the characterization of microscopic objects. To demonstrate an application that takes advantage of the broadband nature of the source, the spectral responses of trapped microspheres in a microfluidic environment were investigated.

The ability to simultaneously manipulate and characterize a single microscopic object is an important functionality for lab-on-a-chip applications (D. L. Yin, E. J. Lunt, M. I. Rudenko, D. W. Deamer, A. R. Hawkins, and H. Schmidt, "Planar optofluidic chip for single particle detection, manipulation, and analysis," Lab Chip 7(9), 1171-1175 (2007)). The platform demonstrated here utilizes both microfluidic flow and optical forces from a broadband source to position dielectric microparticles for individual analysis. Following transport within a microfluidic channel, the particle's position is controlled by optical forces generated by a waveguide's evanescent field. These radiation forces, which are due to changes in the incident light momentum, can be decomposed into transverse and longitudinal components as shown in FIGS. 17a-b. The decay of the evanescent field intensity results in a gradient trapping force that attracts the particle to the waveguide (A. Ashkin, "Forces of a single-beam gradient laser trap on a dielectric sphere in the ray optics regime," Biophys. J. 61(2), 569-582 (1992)). Particle scattering and absorption of the incident light momentum leads to a radiation pressure force that propels the particles in the direction of light propagation (A. Ashkin, "Forces of a single-beam gradient laser trap on a dielectric sphere in the ray optics regime," Biophys. J. 61(2), 569-582 (1992)). Since the trapping light source is broadband, the spectral response of the trapped microparticle can be used to for characterization.

Figure 18:
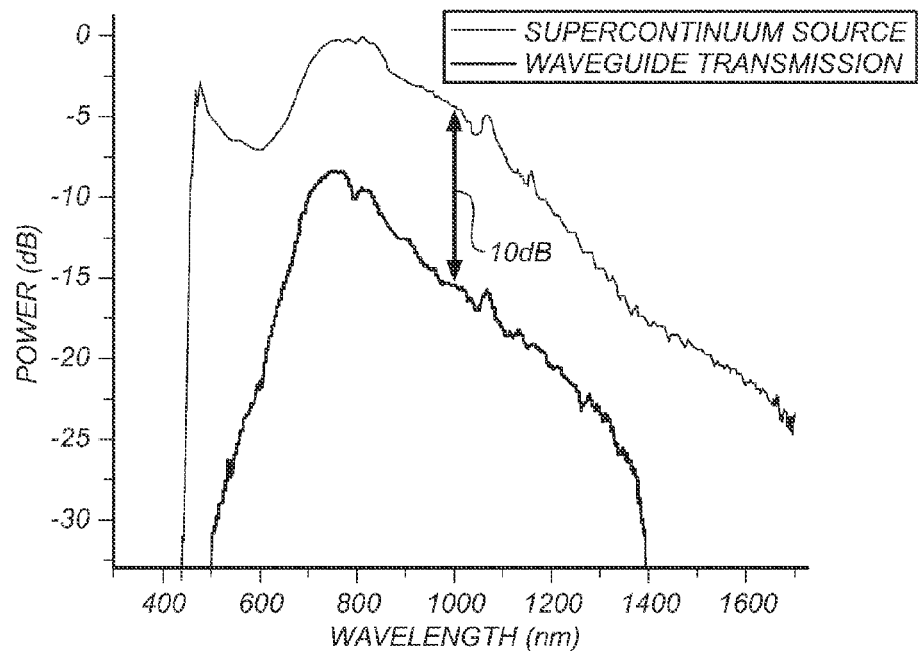

Several design parameters were considered to ensure broadband operation and the generation of strong optical forces. The waveguiding material was stoichiometric silicon nitride ($Si_3N_4$), which has low absorption in the visible and near infrared and allows fabrication of low loss waveguides (A. Gondarenko, J. S. Levy, and M. Lipson, "High confinement micron-scale silicon nitride high q ring resonator," Opt. Express 17(14), 11366-11370 (2009)). Silicon nitride's high refractive index (n=2.0) relative to water (n=1.33) leads to strong gradient trapping forces. The dimensions of the waveguide were 200 nm tall by 2 μm wide and nanotapers at the end of the waveguides ensured that light coupled into the fundamental quasi-TM waveguide mode. The light source was a commercially available supercontinuum (SC) source (Fianium SC-450), which generated a broad output spectrum (500 nm-2.0 μm) and high average powers (~4 Watts). Owing to the source's high degree of spatial coherence (I. Zeylikovich, V. Kartazaev, and R. R. Alfano, "Spectral, temporal, and coherence properties of supercontinuum generation in microstructure fiber," J. Opt. Soc. Am. B-Opt. Phys. 22(7), 1453-1460 (2005)), the SC light can be efficiently focused down by a tapered lens fiber to mode match with the waveguide nanotapers. The input spectrum of the SC source along with the waveguide transmission spectrum is shown in FIG. 18. Only a 10 dB power loss was measured between the input and output of the waveguide while efficiently coupling light at wavelengths across the near infrared spectrum.

6.1.2 Materials and Methods

The optofluidic devices were fabricated using standard microlithography techniques. Details on the waveguide fabrication can be found in A. Gondarenko, J. S. Levy, and M. Lipson, "High confinement micron-scale silicon nitride high q ring resonator," Opt. Express 17(14), 11366-11370 (2009), where the same process was used with demonstrated waveguide propagation losses of 0.1 dB/cm in the near infrared. Microfluidic channels with 30 μm height and 300 μm width were fabricated from polydimethylsiloxane (PDMS). Inlet and outlet ports for fluids were punched through the PDMS and the channels were aligned orthogonal to the waveguide to allow passing microspheres to interact with the waveguide evanescent field.

Broadband light was coupled onto the photonic chip and measuring the waveguide transmission spectrum. The free space output of the SC source was coupled into a single mode polarization maintaining fiber (Thorlabs P5-1550PM). The tapered fiber was butt coupled to the waveguide input and oriented to excite the waveguide quasi-TM mode. The waveguide output was collected with an achromatic microscope objective (Olympus Plan 40×) and passed through a polarization analyzer (Newport 10GL08). The light was then coupled into a multimode fiber and its spectrum measured with a spectrometer (Ocean Optics HR2000). Polystyrene microspheres (Duke Scientific n=1.59) of various diameters were prepared in deionized (DI) water with surfactant to prevent aggregation. The microsphere solution was injected into the microfluidic channels and flow velocity was controlled by adjusting the height of the microsphere solution reservoir.

6.1.3 Results

Figure 19:
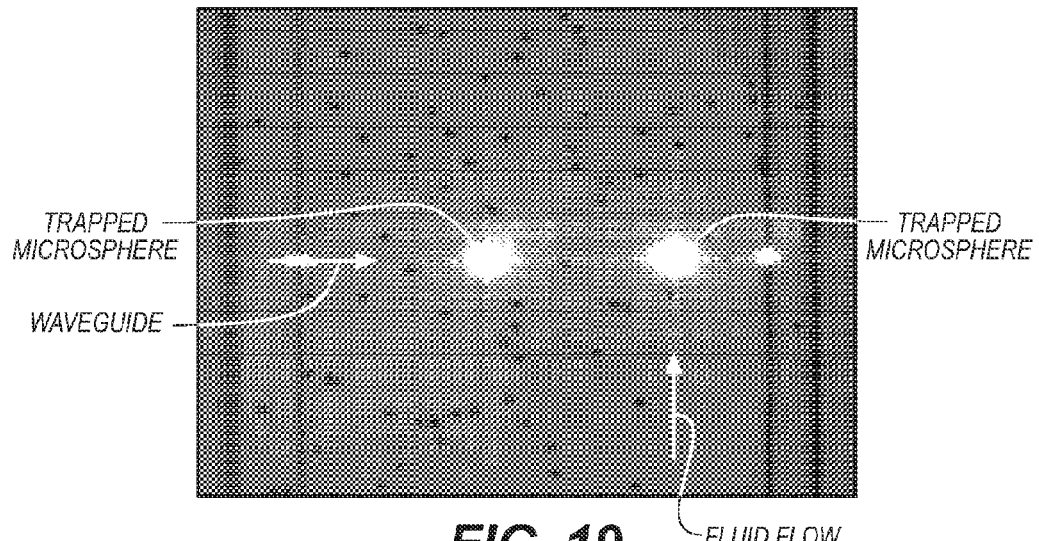

Microspheres of various diameters were flowed through the microfluidic channel and were optically trapped and transported by the waveguide's evanescent field. FIG. 19 shows the manipulation of 3 μm diameter particles using broadband light with ~10 mW of guided power. Optically induced damage to biomolecules should not be a concern for this system owing to the relatively low optical powers used along with operation in the low-absorption near infrared regime (Y. Liu, G. J. Sonek, M. W. Berns, and B. J. Tromberg, "Physiological monitoring of optically trapped cells: Assessing the effects of confinement by 1064-nm laser tweezers using microfluorometry," Biophys. J. 71, 2158-2167 (1996)). Roughly 25% of the microspheres were trapped by the waveguide; this trapping efficiency could be improved by decreasing the channel height, increasing the optical power, or slowing the flow speed.

The optical forces on a polystyrene microsphere were calculated using 3D finite element analysis with the Maxwell stress tensor formalism (B. S. Schmidt, A. H. J. Yang, D. Erickson, and M. Lipson, "Optofluidic trapping and transport on solid core waveguides within a microfluidic device," Optics Express 15(22), 14322-14334 (2007)); the simulated mode results are shown in FIGS. 17a-b. For a 3 μm diameter particle with 5 nm waveguide separation and 850 nm trapping wavelength, the gradient force and scattering force were 1.5 nN/W and 0.21 nN/W respectively. These values were in good agreement with previous results obtained for silicon nitride waveguides (S. Gaugiran, S. Getin, J. M. Fedeli, and J. Derouard, "Polarization and particle size dependence of radiative forces on small metallic particles in evanescent optical fields. Evidences for either repulsive or attractive gradient forces," Optics Express 15, 8146-8156 (2007)). Trapping of microspheres with diameters ranging from 500 nm to 20 microns was observed.

Figure 20:
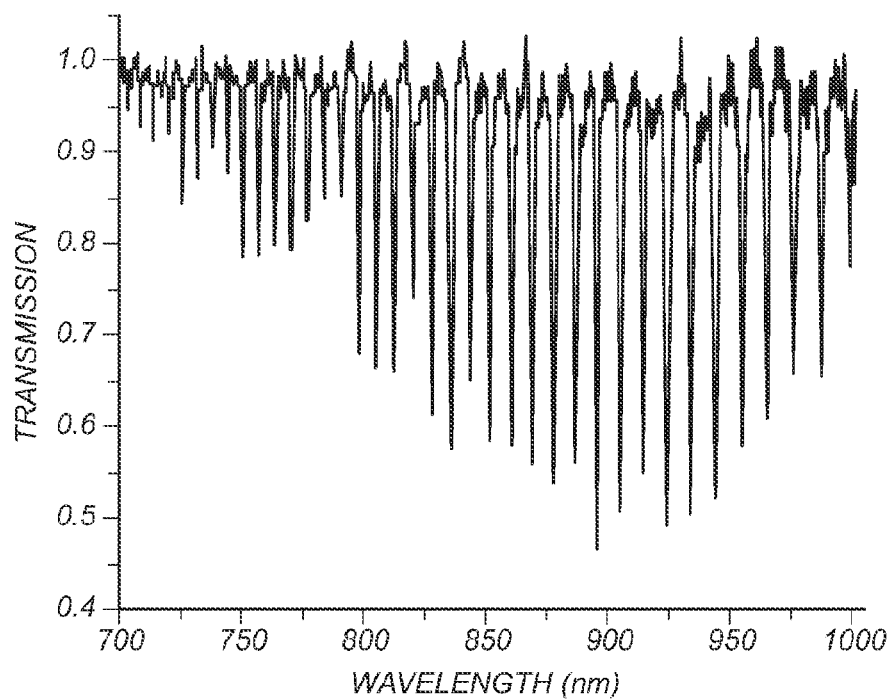

Particles that were trapped by the intensity gradient of the broadband light source could be simultaneously analyzed by measuring the spectrum of the waveguide transmission. FIG. 20 shows the transmission spectrum of the waveguide while an 18 μm polystyrene microsphere was trapped. The curve was normalized to the spectrum when no particle was present. The transmitted spectrum displayed a series of dips that corresponded to the whispering gallery mode (WGM) resonances of the trapped microsphere. Wavelengths that were integer multiples of the microsphere circumference accumulated owing to total internal reflection at the boundaries of the microsphere.

Figure 21:
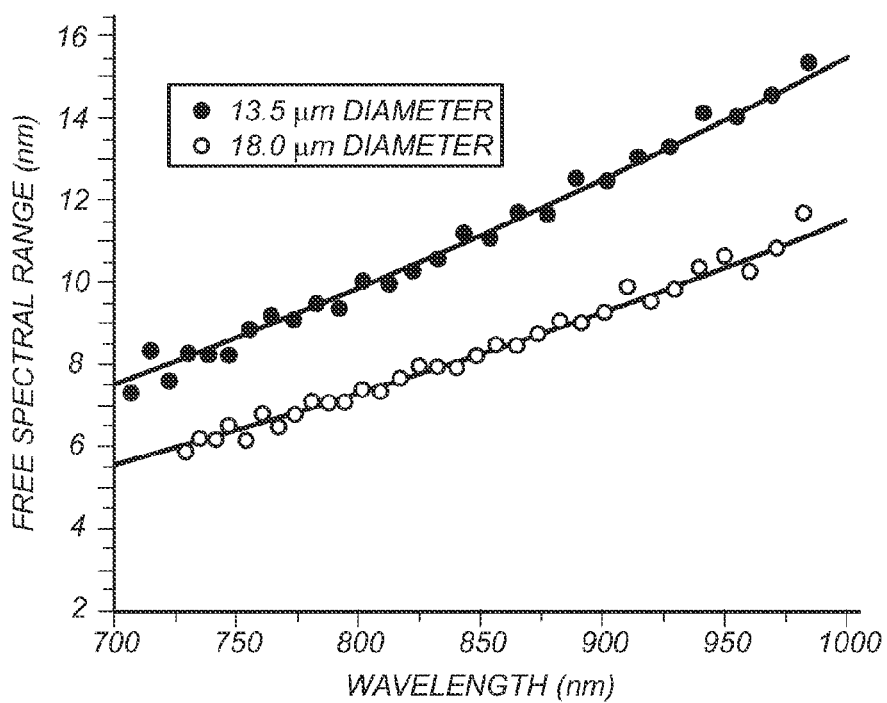

FIG. 21 shows the free spectral range measured using microspheres of different diameters. By controlling the microsphere concentration and fluid flow velocity single microspheres were trapped to simplify the analysis of the transmitted spectra. The solid lines represent the theoretical curves for WGM resonances calculated using the known refractive indices of the materials and the measured size of the particles (C. C. Lam, P. T. Leung, and K. Young, "Explicit asymptotic formulas for the positions, widths, and strengths of resonances in mie scattering," J. Opt. Soc. Am. B-Opt. Phys. 9(9), 1585-1592 (1992)). The agreement between the data and theoretical curves affirmed that light was coupling into the fundamental resonant cavity modes of these microspheres. Therefore, not only was the broadband light being used to physically manipulate the particle, but it also provided a spectral signature of the interaction allowing analysis of the particle. Changes in the resonance wavelength and linewidth can be used to sense changes in the local fluidic environment such as adsorption of biomolecules to the microsphere's surface.

6.1.4 Discussion

This example demonstrates the simultaneous optical trapping, manipulation and analysis of single microscale particles using silicon nitride waveguides and a broadband supercontinuum light source. A white-light source was used for integrated optical trapping, which may enable new lab-on-a-chip biosensors with increased functionalities. Several broadband particle characterization methods can be used in conjunction with the technology demonstrated here, including fluorescence and scattering spectroscopy (P. Li, K. B. Shi, and Z. W. Liu, "Manipulation and spectroscopy of a single particle by use of white-light optical tweezers," Opt. Lett. 30(2), 156-158 (2005)) as well as coherent anti-stokes raman spectroscopy (K. B. Shi, P. Li, and Z. W. Liu, "Broadband coherent anti-stokes raman scattering spectroscopy in supercontinuum optical trap," Appl. Phys. Lett. 90(14), 3 (2007)). Measurements of whispering gallery modes in various structures have successfully been used to detect the binding of single biomolecules (F. Vollmer, D. Braun, A. Libchaber, M. Khoshsima, I. Teraoka, and S. Arnold, "Protein detection by optical shift of a resonant microcavity," Appl. Phys. Lett. 80(21), 4057-4059 (2002)). To date, coupling light into these high quality factor devices is done using a tapered optical fiber or a prism and therefore a complete integrated system cannot be fabricated using standard photolithography techniques. The use of in-plane waveguide excitation of flowing microspheres provides an approach to fully integrate WGM-based biosensors.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. An integrated optofluidic system, comprising:
   one or more functionalized microspheres, wherein each functionalized microsphere comprises an identifier binding ligand configured to bind a decoder binding ligand which binds an analyte;
   a light source configured to produce light over an analytical wavelength range;
   a planar substrate;
   a microfluidic channel integrated on the planar substrate;
   a sensor region fluidically connected to the microfluidic channel, wherein the sensor region comprises an oxide interface; and
   a waveguide integrated with the microfluidic channel through which the light is propagated, wherein the waveguide is configured to transport the one or more functionaiized microspheres to the oxide interface and retain the one or more functionalized microspheres at the oxide interface, wherein the oxide interface intersects the waveguide.

2. The integrated optofluidic system of claim 1 wherein the waveguide optically traps the microspheres in the microfluidic channel.

3. The integrated optofluidic system of claim 1 wherein the microspheres are trapped, stopped or retained within the sensor region.

4. The integrated optofluidic system of claim 3 wherein the trapped microspheres continue to move in the direction of the light propagated through the waveguide.

5. The integrated optofluidic system of claim 1 wherein the light source is a broadband light source and the analytical wavelength range is visible and near-infrared.

6. The integrated optofluidic system of claim 5 wherein the broadband light source produces visible and near-infrared wavelengths simultaneously.

7. The integrated optofluidic system of claim 1 wherein the light source is a supercontinuum light source.

8. The integrated optofluidic system of claim 1 further comprising a spectrometer.

9. The integrated optofluidic system of claim 1 further comprising a sample inlet port wherein the microfluidic channel is fluidically connected to the sample inlet port.

10. The integrated optofluidic system of claim 1 further comprising at least one sample handling well, wherein the at least one sample handling well comprises a well inlet port and a outlet port, and wherein:
    the well inlet port and the well outlet port are fluidically connected to the sample handling well to allow fluid contact between the sample inlet port and the sample handling well; and
    the well outlet port is fluidically connected to the microfluidic channel.

11. The integrated optofluidic system of claim 10 wherein the well inlet port and the well outlet port are the same port.

12. A method of measuring a resonant light scattering signature, comprising:
    optically trapping a functionalized microsphere at an oxide interface of a sensor region with a waveguide, wherein the functionalized microsphere comprises an identifier binding ligand configured to bind a decoder binding ligand which binds an analyte, and wherein the oxide interface intersects the waveguide;
    exciting a resonant light scattering signature of the particle with a light source that produces light over an analytical wavelength range; and
    measuring the resonant light scattering signature of the functionalized microsphere using the waveguide transmission.

13. The method of claim 12 wherein the light source is a broadband light source and the analytical wavelength range is visible and near infrared.

14. The method of claim 13 wherein the broadband light source produces visible and near-infrared wavelengths simultaneously.

15. The method of claim 12 wherein the light source is a supercontinuum light source.

16. A method of measuring a resonant light scattering signature, comprising:
    providing an integrated optofluidic system, wherein the system comprises:
    a planar substrate;
    a microfluidic channel integrated on the planar substrate;
    a sensor region fluidically connected to the microfluidic channel, wherein the sensor region comprises an oxide interface; and
    a waveguide integrated with the microfluidic channel through which light is propagated, wherein the oxide interface intersects the waveguide;
    introducing a functionalized microsphere into the integrated optofluidic system, wherein the functionalized microsphere comprises an identifier binding ligand configured to bind a decoder binding ligand which binds an analyte;
    optically trapping the functionalized microsphere in the sensor region at the oxide interface of the sensor region with the waveguide;
    exciting a resonant light scattering signature of the functionalized microsphere with a light source that produces light over an analytical wavelength range; and measuring the resonant light scattering signature of the functionalized microsphere using the waveguide transmission.

17. The method of claim 16 further comprising, releasing the functionalized microsphere by decreasing optical power or changing the wavelength of the light.

18. The method of claim 16 wherein the light source is a broadband light source and the analytical wavelength range is visible and near-infrared.

19. The method of claim 16 wherein the resonant light scattering signature comprises whispering gallery mode (WGM) resonance.

20. A method of identifying one or more bound analytes, comprising:
  providing an integrated optofluidic system, wherein the system comprises:
  a planar substrate;
  a microfluidic channel integrated on the planar substrate;
  a sensor region connected to the microfluidic channel, wherein the sensor region comprises an oxide interface; and
  a waveguide integrated with the microfluidic channel through which light is propagated, wherein the oxide interface intersects the waveguide;
  providing an identifiable functionalized microsphere that has an affinity for at least one target analyte, wherein the functionalized microsphere comprises an identifier binding ligand configured to bind a decoder binding ligand which binds the at least one target analyte;
  introducing the functionalized microsphere into the integrated optofluidic system;
  transporting the functionalized microsphere to the oxide interface with the waveguide;
  optically trapping the functionalized microsphere at the oxide interface in the sensor region with the waveguide;
  exciting a resonant light scattering signature of the functionalized microsphere with a light source that produces light over an analytical wavelength range, comprising exciting the functionalized microsphere one or more times over a first analytical wavelength range to produce at least one reference resonant light scattering signature for the functionalized microsphere, wherein the reference resonant light scattering signature uniquely identifies the functionalized microsphere;
  measuring the reference resonant light scattering signature of the functionalized microsphere using the waveguide transmission;
  contacting the functionalized microsphere with a sample suspected of containing at least one analyte where, if the analyte is present in the sample, binding occurs between the functionalized microsphere and the at least one analyte;
  scanning the contacted functionalized microsphere one or more times over a second analytical wavelength range to produce at least one binding resonant scattering signature for the contacted functionalized microsphere;
  measuring the binding resonant light scattering signature of the functionalized microsphere using the waveguide transmission;
  detecting binding of the at least one analyte to the contacted functionalized microsphere by comparing differences between the at least one reference resonant light scattering signature and the at least one binding resonant light scattering signature; and
  identifying one or more bound analytes on the basis of the comparison between the at least one reference resonant light scattering signature and the at least one binding resonant light scattering signature.

21. The method of claim 20 wherein the at least one reference resonant light scattering signature and the at least one binding resonant light scattering signature is a WGM resonance.

22. The method of claim 20 wherein the light source is a broadband light source and the analytical wavelength range is visible and near-infrared.

23. The method of claim 21 wherein the broadband light source produces visible and near-infrared wavelengths simultaneously.

24. The integrated optofluidic system of claim 1, wherein the oxide interface is perpendicular to the waveguide.

25. The integrated optofluidic system of claim 1, wherein the microfluidic channel extends between a first oxide clad region and a second oxide clad region, wherein an unclad region extends between the first oxide clad region and the second oxide clad region along the planar substrate, wherein the first oxide clad region and the second oxide clad region are elevated relative to the unclad region, and wherein the oxide interface corresponds to the second oxide clad region.

26. The integrated optofluidic system of claim 1, wherein the oxide interface comprises a glass interface.

27. The integrated optofluidic system of claim 1, wherein the oxide interface comprises silicon dioxide.

* * * * *